United States Patent [19]
Steffee et al.

[11] Patent Number: 5,242,446
[45] Date of Patent: Sep. 7, 1993

[54] CONNECTOR FOR A SPINAL COLUMN CORRECTIVE DEVICE

[75] Inventors: Arthur D. Steffee, Novelty; Frank S. Janson, Rocky River, both of Ohio

[73] Assignee: AcroMed Corporation, Cleveland, Ohio

[21] Appl. No.: 816,102

[22] Filed: Jan. 2, 1992

[51] Int. Cl.⁵ .............................................. A61F 5/00
[52] U.S. Cl. ...................................... 606/61; 606/60; 606/72; 248/231.9
[58] Field of Search .................. 606/60, 61, 72–74, 606/103; 411/395, 400, 401, 383; 248/231.9, 71

[56] References Cited

U.S. PATENT DOCUMENTS

| | | | |
|---|---|---|---|
| 3,997,138 | 12/1976 | Crock et al. | 606/61 X |
| 4,231,247 | 11/1980 | Haydon | 411/400 |
| 4,569,338 | 2/1986 | Edwards | 606/61 X |
| 4,913,134 | 4/1990 | Luque | 606/61 X |

FOREIGN PATENT DOCUMENTS

| | | | |
|---|---|---|---|
| 42219 | 3/1917 | Fed. Rep. of Germany | 248/71 |
| 9106252 | 5/1991 | World Int. Prop. O. | 606/736 |

OTHER PUBLICATIONS

Zimmer Orthopaedic Ad, JBJS, vol. 38B No. 2, May, 1956.

Primary Examiner—Robert A. Hafer
Assistant Examiner—Sam Rimell
Attorney, Agent, or Firm—Tarolli, Surdheim & Covell

[57] ABSTRACT

The present invention relates to an apparatus for connecting a spinal column corrective device to a vertebra. The apparatus comprises a screw threadably engageable with the vertebra. An elongate flexible member extends through an opening in the screw and around at least a portion of the corrective device to connect the corrective device to the vertebra.

4 Claims, 2 Drawing Sheets

CONNECTOR FOR A SPINAL COLUMN CORRECTIVE DEVICE

BACKGROUND OF THE INVENTION

1. Technical Field

The present invention relates to surgically correcting a deformed and/or degenerated spinal column, and particularly, relates to a connector for attaching a corrective device to a vertebra of a spinal column.

2. Description of the Prior Art

Connectors for attaching corrective devices to vertebra of a spinal column are known. U.S. Pat. No. 4,604,995 discloses the use of sublaminar wiring for fixing a spinal column corrective device to the vertebra. In U.S. Pat. No. 4,604,995, wires are passed under and around laminae of the spinal column and then twisted together around the corrective device to connect the corrective device to the vertebra.

SUMMARY OF THE INVENTION

The present invention is directed to an apparatus for connecting a corrective device, such as a bendable elongate rod or bone graft, to a vertebra of a spinal column. The apparatus comprises a screw threadably engageable with the vertebra. An elongate flexible member extends through an opening in the screw and around a portion of the corrective device for connecting the corrective device to the vertebra.

In one embodiment of the present invention, the opening extends along the axis of the screw. Two elongate members extend through the opening. End portions of the elongate members are connected together by sufficient means such as a weld bead. The weld bead has a diameter greater than the diameter of the opening to prevent removal of the elongate members from the opening when the spinal column corrective device is connected to the vertebra. The elongate members may be connected together in any way which prevents the elongate members from being pulled through the opening. End portions of the elongate members are extended around the corrective device and twisted about each other to connect the corrective device to the vertebra.

The screw includes a frustoconical recess having an axis extending along the axis of the opening. The elongate members extend through the opening and the recess. Because of the frustoconical recess, the elongate members do not engage sharp edges which may damage the elongate members.

In another embodiment of the present invention, the opening extends transverse to the axis of the screw. An elongate member extends through the opening. The opposite ends of the elongate member are twisted together around the corrective device to attach the corrective device to the vertebra.

In yet another embodiment of the present invention, the opening extends transverse to the axis of the screw and is oval shaped.

BRIEF DESCRIPTION OF THE DRAWINGS

Further features of the present invention will become apparent to those skilled in the art to which the present invention relates from reading the following specification with reference to the accompanying drawings, in which.

DESCRIPTION OF PREFERRED EMBODIMENTS

A pair of surgically implantable rods 20, (FIG. 1) for correcting deformation and/or degeneration of a human spinal column C are connected with several vertebrae V of the spinal column. Clamps 22, hooks 24 and connectors 28, 30 and 32 embodying the present invention connect the rods 20 with the vertebrae.

Figure 1:
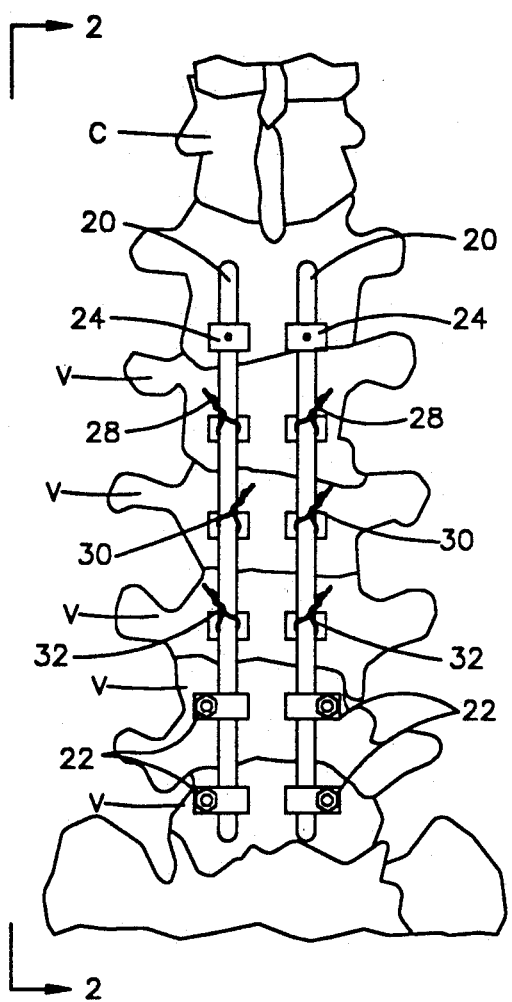
FIG. 1 is a view of a corrective device connected with a portion of a human spinal column by connectors embodying the present invention.
Figure 2:
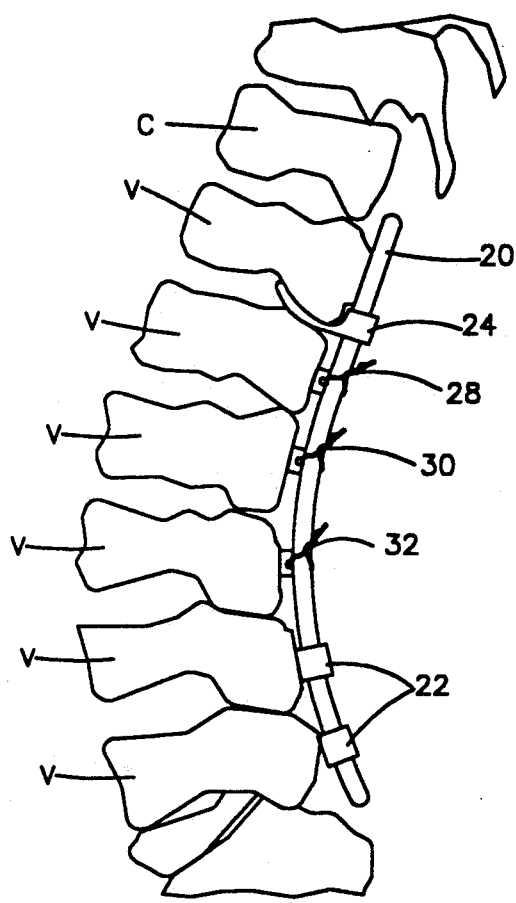
FIG. 2 is a view taken along the line 2—2 in FIG. 1.

Each rod 20 is elongate and has a circular cross-section taken in a plane extending perpendicular to the longitudinal central axis of the rod. The rod 20 is bendable to conform to a desired curvature of the spinal column C, as illustrated in FIG. 2, in any desired plane. The rod 20 has sufficient strength and rigidity to maintain the vertebrae V in the desired relationship. Several of the vertebrae V of the spinal column C are illustrated in FIG. 1, with the spinous processes removed for clarity. Removal of the spinous processes may or may not be necessary during the surgical procedure to implant the rods 20.

Figure 3:
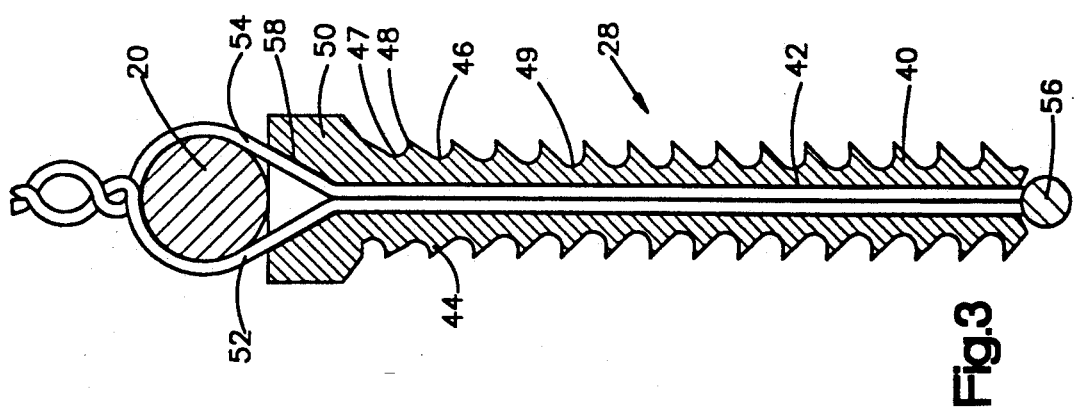
FIG. 3 is a cross-sectional view of one of the connectors shown in FIG. 1.

In one embodiment of the present invention, the connector 28 (FIG. 3) includes a screw 40 threadably engageable with the vertebra V. Threads 44 on the screw 40 have a minor diameter 46 and a major diameter 48 radially outward of the minor diameter. The minor diameter 46 may be tapered along a portion of the screw 40. The minor diameter 46 tapers inward (becomes smaller) from a radially outward minor diameter 47 located near a head 50 of the screw 40 toward a radially inward minor diameter 49 located near a center portion of the screw 40.

The screw 40 has surface means defining an opening 42 extending along the axis of the screw. Flexible, elongate members 52 and 54 extend through the opening 42 in the screw 40. The elongate members 52 and 54 are preferably metal wire. The elongate members 52 and 54 are connected together by any sufficient means, such as a weld bead 56 located adjacent the end portion of the screw opposite the head 50. The weld bead 56 has a diameter which is greater than the diameter of the opening 42 to prevent removal of the elongate members 52 and 54 from the opening 42 when the spinal column corrective device 20 is connected to the vertebra. End portions of the elongate members 52, 54 extend out of the opening 42 and are twisted together around the rod 20 to connect the rod to the vertebra V.

The head 50 of the screw 40 includes a frustoconical recess 58. The members 52 and 54 extend through the opening 42 and through the recess 58. The members 52 and 54 do not engage any sharp edges of the screw 40.

Figure 4:
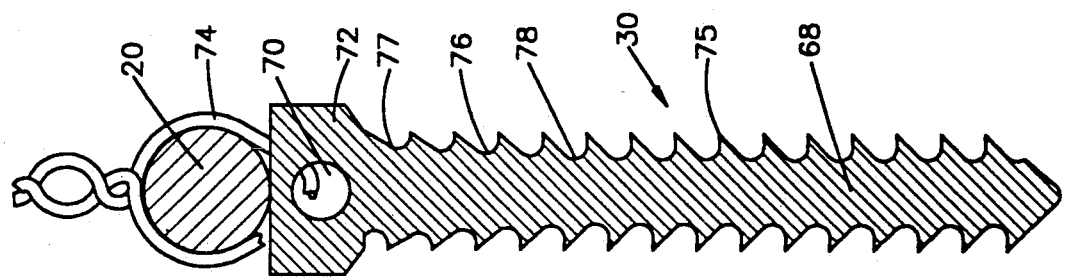
FIG. 4 is a cross-sectional view of a connector according to another embodiment of the present invention.

In another embodiment of the present invention, the connector 30 (FIG. 4) includes a screw 68 threadably engageable with a vertebra V. The screw 68 has surface means defining an opening 70 in a head 72 of the screw. The axis of the opening 70 extends transverse to the longitudinal axis of the screw 68. An elongate member 74 extends through the opening 70 in the screw 68. Opposite end portions of the member 74 are twisted together around the rod 20 to connect the rod with the vertebra V.

The screw 68 also includes threads 75 which have a minor diameter 76 which tapers inward along a portion of the screw 68 in a manner similar to screw 40. The minor diameter 76 tapers from a radially outward minor diameter 77 near the head 72 to a radially inward minor diameter 78 near a center portion of the screw 68.

Figure 5:
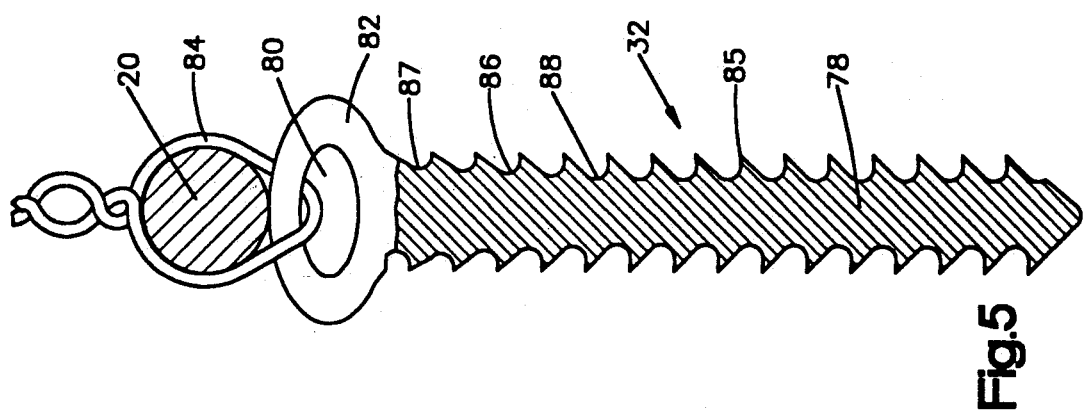
FIG. 5 is a cross-sectional view of a connector according to yet another embodiment of the present invention.

In another embodiment of the present invention, the connector 32 (FIG. 5) includes a screw 78 threadably engageable with the vertebra V. The screw 78 has surface means defining an oval-shaped opening 80 in a head 82 of the screw. The opening 80 has an axis which extends transverse to the longitudinal axis of the screw 70. An elongate member 84 extends through the opening 80 in the screw 70. Opposite end portions of the member 84 are twisted together around the rod 20 to connect the rod with the vertebra V.

The screw 78 also includes threads 85 which have a minor diameter 86 which tapers along a portion of the screw 78 in a manner similar to screws 40 and 68. The minor diameter 86 tapers inward from a radially outward minor diameter 87 near the head 82 to a radially inward minor diameter 88 near a center portion of the screw 68.

The connectors 28, 30 and 32 are screwed into the vertebra V (FIG. 1) into their desired positions. The bendable rods 20 are then positioned above the connectors 28, 30 and 32. Elongate members 52 and 54 of the connector 28 are twisted about the rod 20 to connect the rod to the vertebra V. The two ends of the elongate member 74 are twisted about rod 20 to connect the rod 20 to vertebra V. The two ends of the elongate member 84 of connector 32 are twisted about the rod 20 to connect the rod 20 to the vertebra V.

Although the present invention has been described in conjunction with connecting rods to vertebra, it may be used to connect any other spinal column corrective device such as bone graft to the vertebra V.

From the above description of preferred embodiments of the invention, those skilled in the art may perceive improvements, changes and modifications in the invention. Such improvements, changes and modifications within the skill of the art are intended to be covered by the appended claims.

Having described the invention, the following is claimed:

1. An apparatus for connecting a spinal column corrective device to a vertebra of a spinal column, said apparatus comprising a screw threadably engageable with the vertebra, said screw having means defining an opening extending entirely through said screw and along the longitudinal axis of said screw, and a first elongate flexible member with first and second ends, said first elongate flexible member being extendable through the opening and thus through said screw and around at least a portion of the spinal column corrective device with said first and second ends of said elongate flexible member located outside the opening for connecting the corrective device to the vertebra.

2. An apparatus as set forth in claim 1 further including means preventing removal of said first elongate member from the opening when the spinal column corrective device is connected to the vertebra.

3. An apparatus as set forth in claim 2 further including a second elongate flexible member extendable through the opening, said means preventing removal of said first elongate member being connected to said first and second elongate members.

4. An apparatus as set forth in claim 1 wherein said screw includes a frustoconical recess having an axis extending along the axis of the opening and said elongate member extends through said frustoconical recess.

* * * * *